United States Patent
Klimovitch

(10) Patent No.: US 9,372,126 B2
(45) Date of Patent: Jun. 21, 2016

(54) LOW-COMPLEXITY OPTICAL FORCE SENSOR FOR A MEDICAL DEVICE

(71) Applicant: St. Jude Medical, Atrial Fibrillation Division, Inc., St. Paul, MN (US)

(72) Inventor: Gleb V. Klimovitch, Santa Clara, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 311 days.

(21) Appl. No.: 13/753,400

(22) Filed: Jan. 29, 2013

(65) Prior Publication Data

US 2014/0209797 A1 Jul. 31, 2014

(51) Int. Cl.
| | |
|---|---|
| *G01L 1/24* | (2006.01) |
| *G01B 11/16* | (2006.01) |
| *A61B 19/00* | (2006.01) |

(52) U.S. Cl.
CPC . *G01L 1/24* (2013.01); *G01B 11/16* (2013.01); *A61B 19/46* (2013.01); *A61B 2019/465* (2013.01)

(58) Field of Classification Search
USPC .............. 250/221, 227.14, 227.18, 227.16; 345/173, 175; 385/12, 13, 14, 15, 16, 385/17, 18; 600/587, 405, 490
See application file for complete search history.

(56) References Cited

U.S. PATENT DOCUMENTS

| | | | | |
|---|---|---|---|---|
| 4,420,251 | A * | 12/1983 | James | G01B 11/16 356/32 |
| 5,604,530 | A * | 2/1997 | Saito et al. | 348/70 |
| 5,716,324 | A * | 2/1998 | Toida | 600/160 |
| 2005/0082466 | A1 | 4/2005 | Smith et al. | |
| 2008/0007540 | A1* | 1/2008 | Ostergaard | 345/176 |
| 2008/0051632 | A1* | 2/2008 | Ito | A61B 1/0607 600/114 |
| 2008/0198223 | A1* | 8/2008 | Iriyama | 348/65 |
| 2008/0275428 | A1 | 11/2008 | Tegg et al. | |
| 2009/0247993 | A1 | 10/2009 | Kirschenman et al. | |
| 2010/0094163 | A1 | 4/2010 | Deladi et al. | |
| 2010/0302210 | A1* | 12/2010 | Han et al. | 345/175 |
| 2011/0270046 | A1 | 11/2011 | Paul et al. | |
| 2012/0203169 | A1 | 8/2012 | Tegg | |
| 2012/0330190 | A1 | 12/2012 | Gliner | |

FOREIGN PATENT DOCUMENTS

| | | |
|---|---|---|
| DE | 102009043535 | 3/2011 |
| WO | 2005/011511 | 2/2005 |

OTHER PUBLICATIONS

International Search Report and Written Opinion in PCT Application No. PCT/US2014/012211.

* cited by examiner

*Primary Examiner* — Francis M Legasse, Jr.
(74) *Attorney, Agent, or Firm* — Dykema Gossett PLLC

(57) ABSTRACT

An apparatus for detecting deformation of an elongate body may comprise a light source configured to sequentially provide light of multiple frequencies, an optical receiver configured to receive light from the light source, and a filter disposed between the light source and the optical detector. The filter may comprise multiple segments, each of the segments configured to filter light at one of the frequencies so as to alter the amount of light incident on said optical receiver. A total amount of light detected by the optical receiver may change during the sequence so as to be indicative of deformation of the elongate body.

19 Claims, 4 Drawing Sheets

LOW-COMPLEXITY OPTICAL FORCE SENSOR FOR A MEDICAL DEVICE

BACKGROUND a. Technical Field

The instant disclosure relates to elongate medical devices, such as catheters and introducers, for example. More specifically, the instant disclosure relates to the detection and measurement of external forces on an elongate medical device.

b. Background Art

Catheters are used for an ever-growing number of procedures, including diagnostic and therapeutic procedures. Such procedures involve navigating the catheter through the patient's vasculature to a biological site and, for some procedures and some catheters, initiating and/or maintaining contact between the tip of the catheter and tissue. During such navigation and procedures, it may be desirable to assess the deformation of the catheter tip and/or the force applied to the tip of the catheter to determine if there is contact between the catheter tip and tissue and to ensure that the amount of force does not become so great that the catheter tip inadvertently damages the tissue, such as by puncturing the tissue.

Many systems and methods are known for assessing the force on a catheter tip. However, known systems generally either involve multiple sensors (and thus may be more complicated or larger than desired) or do not detect force with sufficient degrees of freedom (for example, magnitude and/or direction of deflection and/or twisting).

The foregoing discussion is intended only to illustrate the present field and should not be taken as a disavowal of claim scope.

BRIEF SUMMARY

An embodiment of an apparatus for detecting deformation of an elongate body may comprise a light source configured to provide light of multiple frequencies and/or frequency bands, an optical receiver configured to receive light from the light source, and a filter disposed between the light source and the optical receiver. The filter may comprise multiple segments, each of the segments configured to filter light at one of the frequencies so as to alter the amount of light incident on the optical receiver. A total amount of light detected by the optical receiver may be indicative of deformation of the elongate body.

An embodiment of an elongate medical device may comprise an elongate shaft having a distal end portion and a light source configured to provide light of multiple frequencies and/or frequency bands along an optical path, the optical path disposed within the distal end portion of the elongate shaft. The elongate medical device may further comprise an optical receiver configured to receive light projected along the optical path and a filter disposed in the optical path. The filter may comprise multiple segments, each of the segments configured to filter light at one of the frequencies and/or frequency bands so as to reduce the amount of light incident on the optical receiver.

A system for assessing force on a medical device may comprise an electronic control unit (ECU) configured to receive a signal generated by an optical receiver responsive to multiple frequencies of light, the multiple frequencies and/or frequency bands of light received by the optical receiver in a predetermined sequence, and process the signal in accordance with the predetermined sequence to determine an external force applied to the medical device.

DETAILED DESCRIPTION OF THE DRAWINGS

Various embodiments are described herein with respect to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
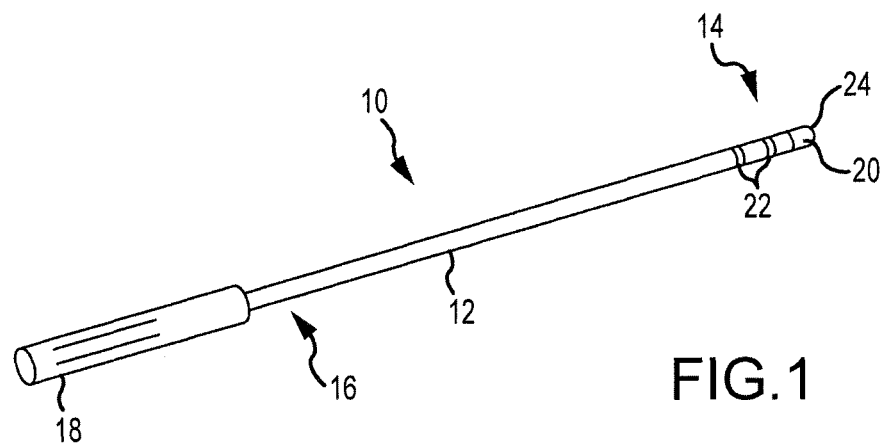
FIG. 1 is an isometric view of an elongate medical device.

Referring now to the Figures, in which like reference numerals refer to the same or similar features in the various views, FIG. 1 is an isometric view of an embodiment of an elongate medical device 10 that may include a low-complexity optical force sensor. The elongate medical device 10 may comprise, for example, a diagnostic and/or therapy delivery catheter, an introducer or sheath, or other like devices. For purposes of illustration and clarity, the description below will be with respect to an embodiment wherein the device 10 comprises a catheter (i.e., catheter 10). It will be appreciated, however, that embodiments wherein the device 10 comprises elongate medical devices other than a catheter remain within the spirit and scope of the present disclosure.

The catheter 10 may comprise a shaft 12 having a distal end portion 14 and a proximal end portion 16. The catheter 10 may be configured to be guided through and disposed in the body of a patient. Accordingly, the proximal end portion 16 may be coupled to a handle 18, which may include features to enable a physician to guide the distal end portion 14 to perform a diagnostic or therapeutic procedure such as, for example only, an ablation procedure on the heart of the patient. Accordingly, the handle 18 may include one or more manual manipulation mechanisms such as, for example, rotational mechanisms and/or longitudinal mechanisms, coupled to pull wires for deflecting the distal end portion 14 of the shaft 12. Exemplary embodiments of manipulation mechanisms, pull wires, and related hardware can be found, for example only, in U.S. patent application publication no. 2012/0203169, hereby incorporated by reference in its entirety. The handle 18 may further include one or more electromechanical connectors for coupling to a mapping and navigation system, an ablation generator, and/or other external systems. For example, an electromechanical connector may provide a connection between an optical force sensor disposed in the catheter 10 and an external electronic control unit (see FIG. 6). The handle 18 may also include one or more fluid connectors for coupling to a source and/or destination of fluids such as, for example only, a gravity feed or fixed or variable-rate pump.

The distal end portion 14 of the shaft 12 may include a number of electrodes 20, 22 for applying ablation energy to tissue, acquiring electrophysiology data from tissue, determining the position and orientation (P&O) of the shaft 12, and/or other purposes known in the art. In an embodiment, the electrode 20 may be a distal tip electrode 20 disposed on a distal tip 24 of the shaft 12, and the electrodes 22 may be ring electrodes 22. The electrodes 20, 22 may be coupled to electrical wiring within the shaft 12, which may extend to the handle 18 and to electromechanical connectors for coupling to external systems, as described above.

The distal end portion 14 may also include one or more fluid ports or manifolds for distributing or collecting fluids such as, for example only, irrigation fluid during an ablation procedure. The fluid ports may be fluidly coupled with one or more fluid lumens extending through the shaft 12 to the handle 18 and a fluid connector for coupling to external fluid sources and/or destinations, as described above. One or more lumens may also be provided through the shaft 12 for passing a second elongate medical device therethrough. In some embodiments, for example, the elongate medical device 10 comprises an introducer that includes at least one lumen configured to receive another device such as a catheter or probe.

The shaft 12 may also include a number of other features, such as one or more electromagnetic sensors for position and navigation, temperature sensors, and other sensors known in the art. One such sensor type that may be included may be for detecting the contact force between the distal tip 24 and tissue. The contact force may be assessed, for example, to ensure that the distal end portion 14 does not apply excessive force to tissue so as to inadvertently puncture or otherwise damage the tissue, to determine if contact is sufficient for an ablation procedure, and/or other purposes known in the art. In an embodiment, the distal end portion 14 may include an optical force sensor, as will be described in conjunction with FIGS. 2-8.

Figure 2:
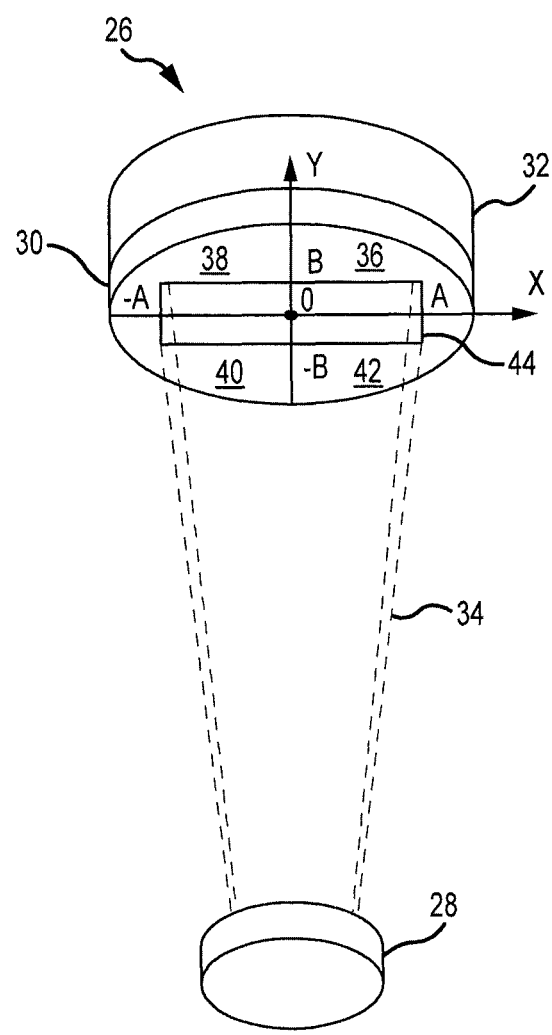
FIG. 2 is a diagrammatic view of an embodiment of an optical force sensor that may be used with the elongate medical device of FIG. 1.

FIG. 2 is a diagrammatic view of an embodiment of an optical force sensor 26. The force sensor 26 may include a light source 28, an optical filter 30, and an optical receiver 32. The light source may project light along an optical path 34 towards the filter 30 and receiver 32. Referring to FIGS. 1 and 2, the force sensor 26 may be disposed in an elongate medical device, such as the catheter 10, for determining the deflection characteristics of the catheter 10 and, in turn, the external force applied to the catheter 10.

The force sensor 26 (i.e., the light source 28, optical filter 30, and optical receiver 32) may be secured within the shaft 12 or other device using techniques known in the art. In an embodiment, the force sensor 26 may be disposed in the distal end portion 14 of the shaft 12. For example, the force sensor 26 (i.e., one or more of the light source 28, the filter 30, and the optical receiver 32) may be placed within about 0.5 inches to about 2 inches of the distal tip 24. In an embodiment, the force sensor 26 may be secured within the shaft 12 such that the light source 28, optical filter 30, optical receiver 32, and optical path 34 are insulated or sealed from fluid.

The light source 28 may include, in an embodiment, a light source configured to output light of multiple different frequencies. For example, the light source 28 may include a multi-color light-emitting diode (LED)—i.e., a single apparatus having multiple LEDs, each capable of emitting light of a particular frequency and/or frequency band, as known in the art. In an embodiment, the light source 28 may include a multi-color LED configured to output three or four colors of light, such as red, blue, green, and yellow. A multi-color LED configured to output fewer, more, and/or different colors may be used in addition or alternatively, in an embodiment.

In an embodiment, a multi-color LED may be chosen for the light source 28 because it is "mechanically single"—i.e., a single die, package, chip or apparatus—yet capable of outputting multiple frequencies of light, as described above. In an embodiment, a mechanically-single light source 28 other than a multi-color LED may be included in the light source 28. Light from the light source 28 may be output in a beam having a substantially circular, elliptical, square, rectangular, or other shape. For reasons that will be explained below, it may be advantageous, in an embodiment, for the light source 28 to output a non-circular projection on the filter 30 such as an elliptical or rectangular shape.

Although the light source 28 will be described with reference to a multi-color LED, other light sources may be used. Furthermore, although different "colors" of light will be described, it should be understood that "color" is merely used as a proxy herein for a particular frequency and/or frequency band of light. In an embodiment, one or more frequencies of light output by the light source 28 may be in some part of the electromagnetic spectrum other than visible light. Furthermore, the light source 28 may be configured to output any number of frequencies and/or frequency bands of light.

The optical filter 30 may comprise a number of segments 36, 38, 40, 42, each configured to filter a particular color of light. For example, a first filter segment 36 may be configured to filter blue light, a second filter segment 38 may be configured to filter green light, a third filter segment 40 may be configured to filter yellow light, and a fourth filter segment 42 may be configured to filter red light. Though each filter segment 36, 38, 40, 42 is described herein with reference to filtering a particular color, it should be understood that, again, color is merely used as a proxy for light frequency. Just as the light source 28 may be configured to output one or more frequencies of light in the non-visible portions of the spectrum, one or more of the filter segments 36, 38, 40, 42 may be configured to filter light frequencies in the non-visible portions of the spectrum.

Filter, as used herein, may be used to refer to passing or rejecting (in a relative sense, as explained below) a particular frequency or set of frequencies. In an embodiment, each segment 36, 38, 40, 42 of the filter 30 may be configured to pass a single frequency of light and/or frequency band of light and substantially reflect and/or absorb the remaining frequencies. In an embodiment, a particular filter segment need not be a perfect or ideal filter—i.e., it need not pass 100% of the desired frequency while rejecting 100% of undesired frequencies. Instead, in an embodiment, it may be sufficient for each filter segment 36, 38, 40, 42 to merely provide a substantial difference between the amount of a desired light at a particular frequency that is passed and the amount of undesired light at other frequencies that is passed. In an embodiment, it may be sufficient, for example, for a filter segment 36, 38, 40, 42 to pass 60% or more of light of a desired frequency or frequency band and 40% or less of light of undesired frequencies or frequency bands. Of course, more discerning filter segments 36, 38, 40, 42 may be used, in an embodiment. For example, in an embodiment, one or more of the filter segments 36, 38, 40, 42 may pass about four times as much of a desired frequency and/or frequency band than of other frequencies produced by the source 28. In another embodiment, one or more of the filter segments 36, 38, 40, 42 may pass about seven times as much of a desired frequency than of other frequencies and/or frequency bands.

Each filter segment 36, 38, 40, 42 may comprise a plastic or polymer sheet, wafer, or other structure. The filter segments 36, 38, 40, 42 may also comprise glass or another material known in the art for light filtering, and may include one or more layers of one or more materials. Furthermore, the different segments 36, 38, 40, 42 may comprise different materials, in an embodiment.

Though the filter 30 is illustrated and described in terms of an embodiment having four segments 36, 38, 40, 42, 44, more or fewer than four segments may be included in the filter 30. In an embodiment, the number of segments in the filter 30 may be equal to or greater than the number of colors of light output by the light source 28. Furthermore, although the segments 36, 38, 40, 42 are shown as occupying equal quadrants of the filter 30, alternative filter arrangements are possible.

The optical receiver 32 may comprise a light detector configured to generate an output signal according to the amount or intensity of light impinging on the receiver 32. In an embodiment, the receiver 32 may be roughly or approximately frequency-indifferent—i.e., substantially equally responsive to light of all frequencies and/or frequency bands output by the light source 28. For example, the receiver 32 may be equally or approximately equally responsive to all frequencies of light in the visible spectrum, in an embodiment.

The filter 30 and receiver 32 may be of substantially the same size and shape and may be oriented substantially perpendicular to the optical path 34, in an embodiment. As shown in FIG. 2, the filter 30 and receiver 32 may be substantially circular. The filter 30 and receiver 32 may have different shapes in other embodiments.

In operation, the light source 28 may provide light of multiple frequencies along the optical path 34, which may be filtered by the segments 36, 38, 40, 42 of the filter 30 and detected by the optical receiver 32. In an embodiment, different colors of light may be transmitted by the light source 28 in a predetermined sequence—i.e., a first color for a first period of time, then a second color for a second period of time, and so on. According to the deflection, twisting, and/or other deformation of the portion of the shaft 12 (or other device) in which the optical path 34 is disposed, the amount of light impinging on a given segment 36, 38, 40, 42 of the filter 30 may change. Because the different segments 36, 38, 40, 42 may filter different colors, as the amount of light impinging on the segments 36, 38, 40, 42 changes as the shaft 12 deforms, the amount of light reaching the receiver 32 will change as different colors of light are provided. Accordingly, by assessing the amount of light detected by the receiver 32 at any given time, in conjunction with the knowledge of what color of light is transmitted by the light source at that time, the deflection, twisting, and/or other deformation characteristics of the portion of the shaft 12 (or other device) in which the optical path 34 is disposed can be determined. Based on the deflection, twisting, and/or other deformation, the exterior force on the distal tip 24 can be determined. The mathematical operations behind these determinations will be described more fully below, following examples of shift and rotation of incident light on the filter 30 and receiver 32.

Compression and expansion of the optical path 34 (i.e., of the portion of the shaft 12 in which in the optical path 34 is disposed) can also be detected by an embodiment the sensor 26. For example, an aperture or other structure may be placed between the light source 28 and the receiver 32 such that compression or expansion of the shaft 12 (i.e., a change in the distance between the light source 28 and the receiver 32) results in a change in the total amount or intensity of light on all segments 36, 38, 40, 42. By measuring this total change, compression or expansion of the shaft 12 can be detected and quantified.

The neutral-state (i.e., undeformed state of the portion of the shaft 12 in which the force sensor 26 is disposed) distance between the light source 28 and the receiver 32 and the relative orientations of the light source 28 and the receiver 32 may be determined according to the bending characteristics of the shaft 12. In general, for reasons explained below, an excess of bending of the portion of the shaft 12 in which the sensor 26 is disposed may reduce the effectiveness of the sensor 26. Accordingly, as the stiffness of the device in which the sensor 26 is disposed increases (and thus the ability of a small section of the device to bend beyond the effective range of the sensor 26 decreases), the distance between the light source 28 and the receiver 32 may also increase. In an embodiment, the light source 28 may be placed about 0.5 inches to about 2 inches from the receiver 32.

Figure 3:
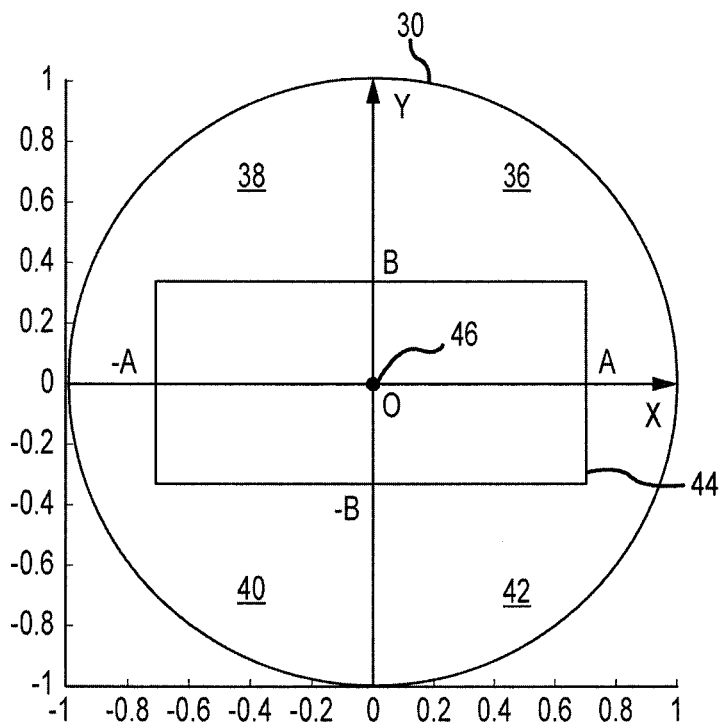
FIG. 3 is a diagrammatic view of an optical filter of the optical force sensor of FIG. 2 with a light beam projection incident thereon.
Figure 4:
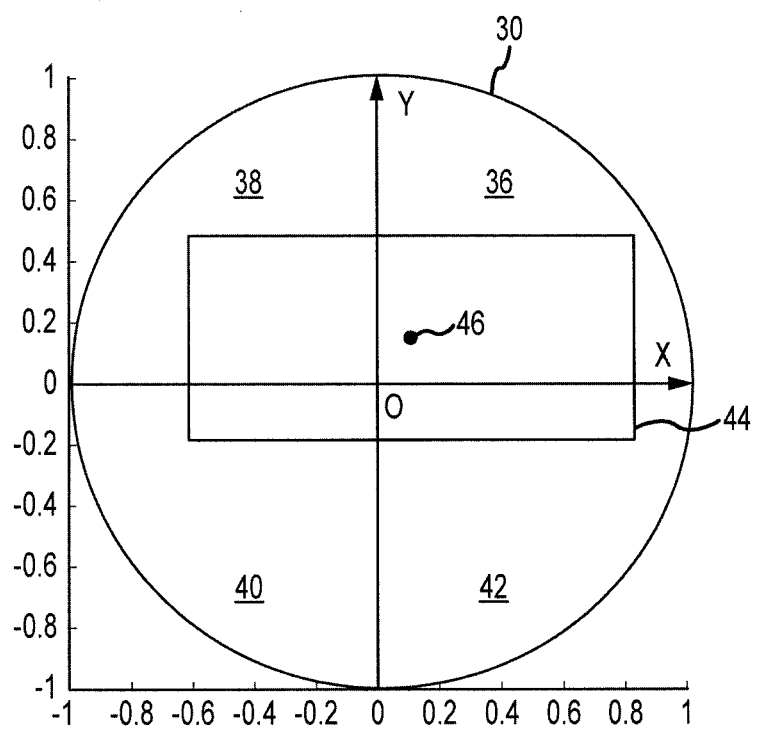
FIG. 4 is a diagrammatic view of the optical filter of FIG. 3, with the incident light beam projection shifted on the optical filter.
Figure 5:
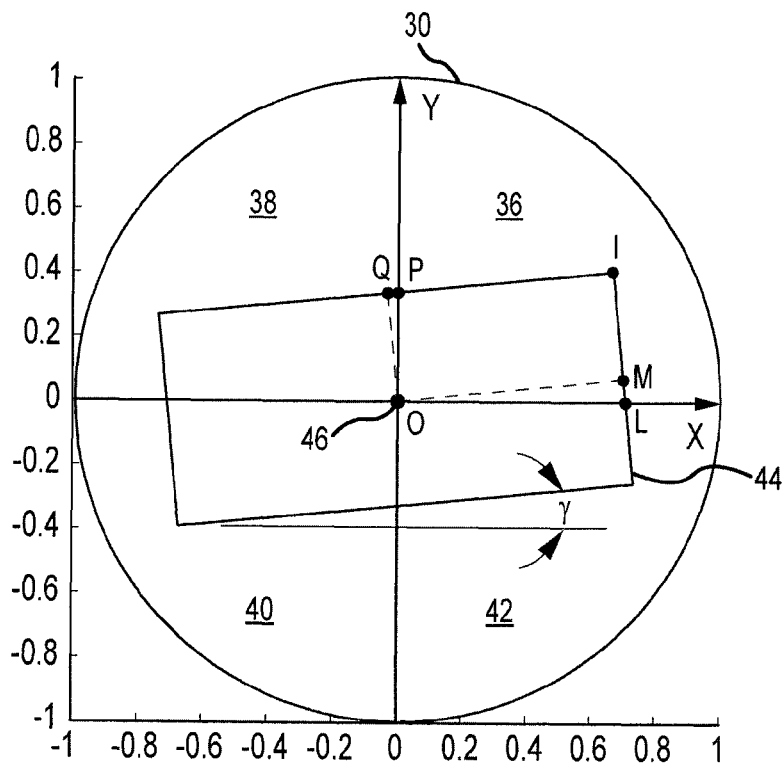
FIG. 5 is a diagrammatic view of the optical filter of FIG. 3, with the incident light beam projection rotated on the optical filter.

FIGS. 3-5 are diagrammatic views of the filter 30 with incident light 44 of a rectangular shape projected thereon from the light source 28. As noted above, the beam projection from the light source 28 may also be substantially square, circular, elliptical, or in some other shape (e.g., asymmetric)—the incident light 44 may thus also be in some other shape. FIGS. 3-5 also show a center point 46 indicating the geometric center of the incident light 44, an X-axis, and a Y-axis, though it should be understood that such labels are provided for explanatory purposes only.

In FIG. 3, the incident light 44 is projected equally upon the four segments 36, 38, 40, 42 of the filter 30 with the center point 46 of the beam projection coincident with the origin O of the X-Y axis, indicating a non-deflected state of the light source 28 relative to the filter 30 (and thus a non-deflected state of the portion of the shaft 12 in which the sensor 26 is disposed). FIG. 4 illustrates the incident light shifted along both the X and Y axes, with the center point 46 within the first filter segment 36, indicating a deflected state of the light source 28 relative to the filter 30. FIG. 4 may represent, for example, a situation in which the shaft 12 is slightly bent or displaced as a result of contact of the device 10 with adjacent tissue, resulting in a shift in the center point 46 of the incident light projection 44 on the filter 30. FIG. 5 illustrates the incident beam projection rotated about the origin of the X-Y axis, indicating a rotated state of the light source 28 relative to the filter 30. FIG. 5 may represent, for example, a situation in which the shaft 12 is twisted, resulting in a concomitant rotation of the incident light beam projection 44 on the filter 30.

As the incident light shifts and/or rotates, the respective amounts of light through the different filter segments 36, 38, 40, 42 change. The sensor 28 takes advantage of this by projecting different colors of light in a predetermined sequence, with each color corresponding to one or more of the filter segments 36, 38, 40, 42. Accordingly, in a deflected or rotated state (such that the amount of incident light 44 is not equal across all filter segments 36, 38, 40, 42), the amount of light incident on the optical receiver 30 will change between different transmitted colors. Due to this change, the deflection and/or rotation of the light source 28 relative to the filter 30 and receiver 32 (and thus the deflection and/or rotation of the portion of the shaft 12 in which the sensor 26 is disposed) can be determined. Illustrative examples follow.

Example—Deflection in Two Dimensions

An embodiment of the sensor 26 may be used to measure deformation with two degrees of freedom—deflection of the shaft 12, and more specifically the distal end portion 14, in two dimensions (i.e., along the X- and Y-axes as shown in FIGS. 3-5). In such an embodiment, the light source 28 may be configured to output two colors of light. For example, the light source 28 may be a two-color LED configured to output blue light and red light.

When the shaft 12 is in a non-deflected state, the light source 28 projects rectangular incident light 44 onto the filter 30, with the center point 46 coincident with the center of the filter and origin of the arbitrarily-assigned X-Y coordinate system. In the rectangular coordinates of FIGS. 3-5, the incident light 44 extends between (−A) and A in the X-direction and between (−B) and B in the Y-direction.

Let the intensity of light incident onto the filter be uniform across and throughout the incident light 44. The products of incident (onto the filter 30) light intensity, filter segment 36, 38, 40, 42 transmission coefficient, and sensitivity per unit area of the receiver 32 can be denoted as $v_{1R}$ and $v_{1B}$ for red and blue light, respectively, passing through the first filter segment 36, $v_{2R}$ and $v_{2B}$ for the second filter segment 38, $v_{3R}$ and $v_{3B}$ for the third filter segment 40, and $v_{4R}$ and $v_{4B}$ for the fourth filter segment 42. As used herein, the subscript R refers to red light, and the subscript B refers to blue light.

In an embodiment, the second filter segment 38 may preferably pass red light (i.e., the second filter segment 38 may prefer, or pass, more red light than another color or set of colors), the fourth filter segment 42 may preferably pass blue light, and the first and third filter segments 36, 40 may equally pass red and blue light. Of course, other distributions of filter segments 36, 38, 40, 42 may be used in an embodiment, and one of skill in the art could readily adapt the equations presented below to a different arrangement of filter segments 36, 38, 40, 42.

The output of the optical receiver 32 for red light in a non-deflected state, $V_{det\_R0}$, may be defined as:

$$V_{det\_R0} = AB(v_{1R} + v_{2R} + v_{3R} + v_{4R}) \quad (1)$$

and the output of the optical receiver 32 for blue light in a non-deflected state, $V_{det\_B0}$ may be defined as:

$$V_{det\_B0} = AB(v_{1B} + v_{2B} + v_{3B} + v_{4B}) \quad (2)$$

where the subscript "0" indicates a neutral state throughout this disclosure—here, zero deflection.

To separately measure red and blue light detected by the optical receiver, red and blue light may be transmitted and detected in a time-multiplexed arrangement. The light source 28 may first output blue light, and the output of the optical receiver 32 may be stored or processed as blue light output. The light source 28 may then output red light, and the output of the optical receiver 32 may be stored or processed as red light output. The respective periods of time for which red and blue light may be output may each be on the order of milliseconds, in an embodiment, though the application of the sensor 26 is certainly not so limited. The respective periods of time may be the same as each other, or may be different from each other.

As a result of deflection of the shaft 12, the incident light 44 may maintain substantially the same shape and orientation, but may shift by Δx and Δy in the X- and Y-directions, respectively, as shown in FIG. 4. Given such a shift, the output of the receiver 32 for a single color may be:

$$V_{det_i} = v_{1i}(A+\Delta x)(B+\Delta y) + v_{2i}(A-\Delta x)(B+\Delta y) + v_{3i}(A-\Delta x)(B-\Delta y) + v_{4i}(A-\Delta x)(B-\Delta y) \quad (3)$$

where i=R or B.

Assuming that Δx and Δy are much smaller than A and B, it can be assumed that equation (3) above is linear (i.e., that the products of Δx and Δy in the various terms of equation (3) are negligible). In this regard, it should be understood that the shift illustrated in FIG. 4 is exaggerated for clarity of illustration. Under such an assumption, and given $V_{det\_R0}$ and $V_{det\_B0}$, equation (3) may reduce to:

$$V_{det_i} = V_{det\_i0} + (v_{1i} - v_{2i} - v_{3i} + v_{4i})(B\Delta X) + (v_{1i} + v_{2i} - v_{3i} - v_{4i})(A\Delta y) \quad (4)$$

where i=R or B, again. It should be noted that equation (4) may also work with an elliptical beam of incident light, rather than a rectangular beam 44.

Equation (4) can be solved with high accuracy for Δx and Δy (i.e., a magnitude and direction thereof) if the values of the coefficient matrix of the right hand side of equation (4) do not differ by more than a factor of 3. That coefficient matrix, referred to below as $v_{mat1}$, characterizes the relationship between Δx, Δy, and $V_{det\_R}$, $V_{det\_B}$ and is shown in equation (5) below:

$$v_{mat1} = \begin{bmatrix} v_{RX} & v_{RY} \\ v_{BX} & v_{BY} \end{bmatrix} \quad (5)$$

where $v_{RX}=v_{1R}-v_{2R}-v_{3R}+v_{4R}$, $v_{RY}=v_{1R}+v_{2R}-v_{3R}+v_{4R}$, $v_{BX}=v_{1B}-v_{2B}-v_{3B}+v_{4B}$, and $v_{BY}=v_{1B}+v_{2B}-v_{3B}+v_{4B}$. Thus, it should be noted that in $v_{mat1}$, the subscript X to the X-direction shown in FIGS. 3-5.

Series of equations (4) will result in two equations (one for blue light, one for red) and two unknowns (Δx and Δy). Accordingly, Δx and Δy may be determined according to known systems and methods for solving a system of several equations with several unknowns.

Once Δx and Δy are determined, the deflection of the shaft 12 over the optical path 44 may be determined. For small deformations (i.e., small degrees of deflection), the angles α, β of deflection in the X- and Y-directions, respectively, are proportional to Δx and Δy, respectively. If the coefficient of proportionality between α and Δx is $\mu_\alpha$ and the coefficient of proportionality between β and Δy is $\mu_\beta$, then the column vector with components (α, β) is given by the following matrix equation (6):

$$\begin{pmatrix} \dfrac{\alpha}{\mu_\alpha} \\ \dfrac{\beta}{\mu_\beta} \end{pmatrix} = \text{inv}(v_{mat1}) \begin{pmatrix} V_{det\_R} - V_{det\_R0} \\ V_{det\_B} - V_{det\_B0} \end{pmatrix} \quad (6)$$

where α and β are expressed in radians and inv represents matrix inversion.

The coefficients of proportionality $\mu_\alpha$, $\mu_\beta$ may be determined approximately according to the design of the shaft 12, and may be determined more precisely through a calibration process. For example, one potential calibration procedure may include deflecting the shaft 12 in a number of known deflections (i.e., with known α and β), measuring $V_{det\_R}$ and $V_{det\_B}$ and setting $\mu_\alpha$ and $\mu_\beta$ using equation (6).

For simplicity of calculation and demonstration, the above equations (1)-(6) include assumptions that incident light 44 is coincident on the filter 30 for both blue and red light, that the shape and size of incident light 44 does not change with deflection of the shaft 12, and that light intensity is uniform across and throughout the incident light 44. In real applications, these assumptions do not need to hold. Instead, it may be necessary for only two assumptions to hold for the calculation of α, β according to equations (1)-(6) to be accurate. First, deflection of the shaft 12 (i.e., of the light source 28 relative to the filter 30) must be small enough for the linearity of equation (4) to apply. In an embodiment, this may include deflection of up to about 15°. Second, the changes in output from the receiver 32 for blue light and red light must not be linearly dependent.

From the deflection angles α, β, the exterior forces applied to the distal tip 24 can be calculated. Under normal operating conditions of the catheter 10, deformations such as deflection, twist, and compression are sufficiently small for linear elastostatics to apply. Elastostatics is the study of linear elasticity under the conditions of equilibrium, in which all forces on an elastic body (i.e., the shaft 14) sum to zero, and the deformations are not a function of time.

Linear elasticity models materials as continua. The fundamental "linearizing" assumptions of linear elasticity are small deformations (or strains) and linear relationships between the components of stress and strain. The equilibrium equations of elastostatics that may be used to calculate forces on the distal tip 24 according to calculated deformation are given by equations (7)-(9) below. Equation (7) is the linear elasticity equation of motion:

$$\sigma_{ji,j} + F_i = \rho d_{tt} u_i \quad (7)$$

where $\sigma_{ji}$ is the Cauchy stress tensor (i.e., a tensor matrix having i rows and j columns), the j subscript stands for the partial derivative over the j-th spatial coordinate, $F_i$ is the i-th component of the local body force per unit volume, ρ is the local mass density, $u_i$ is the displacement component along the i-th spatial coordinate of a rectilinear reference frame (the directions of which may, but do not need to, coincide with directions corresponding to deflections α, β) and $d_{tt}$ indicates $$\frac{d^2}{dt^2}.$$

Equation (7) results in three independent equations with six unknowns.

Equation (8) is the linear elasticity strain-displacement equation:

$$\varepsilon_{i,j} = \frac{u_{j,i} + u_{i,j}}{2} \quad (8)$$

where $\epsilon_{i,j}$ is the strain and u is again displacement. Equation (8) results in 6 independent equations with nine unknowns.

Equation (9) is the constitutive equation:

$$\sigma_{ij} = C_{ijkl} \epsilon_{kl} \quad (9)$$

where $C_{ijkl}$ is the stiffness tensor, which is based on the material characteristics of the shaft. Once the Cauchy stress tensor $\sigma_{ji}$ is calculated, the force/torque surface density distribution over the catheter surface is obtained therefrom. Equation (9) results in six independent equations with no additional unknowns.

Equations (7)-(9) give a series of fifteen equations with fifteen unknowns. Methods are known in the art for solving a series of independent equations with an equal number of unknowns. By applying one or more of such known methods, the forces on the distal tip 24, or other portion of the shaft 12 in which the sensor 26 is disposed, can be calculated.

Example—Deflection in Two Dimensions and Twisting

An embodiment of the sensor 26 may be used to measure deformation with three degrees of freedom—deflection of the shaft 12, and more specifically the distal end portion 14, in two dimensions (i.e., along the X- and Y-axes as shown in FIGS. 3-5), as well as twisting about an axis (i.e., rotation of the light source 28 relative to the filter 30 about an axis that is perpendicular to the X-Y plane in FIGS. 3-5) (i.e., about the beam axis). Such an axis may be, in an embodiment, the axis of the shaft 12. In such an embodiment, the light source 28 may be configured to output three colors of light, such as red, blue, and green.

As noted above, when the shaft 12 is in a non-deflected state, the light source 28 projects a rectangular incident light projection 44 onto the filter 30, with the center point 46 coincident with the center of the filter and origin O of the arbitrarily-assigned X-Y coordinate system (see FIG. 3). In the rectangular coordinates of FIGS. 3-5, the incident light 44 extends between (−A) and A in the X-direction and between (−B) and B in the Y-direction.

While deflection of the shaft 12 may shift the position of incident light 44 as shown in FIG. 4 and as discussed above, twisting of the shaft 12 may rotate the light source 28 relative to the filter 30, and thus rotate the incident light beam 44, as shown in FIG. 5. Let the angle of rotation be γ. Output of the receiver may be $V_{det\_B}$ for blue light, $V_{det\_R}$ for red light, and $V_{det\_G}$ for green light. Once again, the output of the receiver may be generically referred to as $V_{det\_i}$ with i=R, G, B. According to equations (1) and (2) above, and a third equation substantially the same as equations (1) and (2) for green light, the zero-deflection, zero-twist outputs of the receiver $V_{det\_B0}$, $V_{det\_R0}$, $V_{det\_G0}$ may be determined. The effect of deflection on $V_{det\_i}$ in the X- and Y-directions may be accounted for by equation (4). An additional term may then be added to $V_{det\_i}$ to account for twist, as discussed below.

Referring to FIG. 5, let the four corners of the incident light 44 on the first filter portion 36 be O (the origin), L (the point at which the incident light beam projection 44 crosses the X axis), I (the vertex of the incident light 44 in the first filter portion 36), and P (the point at which the incident light 44 crosses the Y-axis). The portion of the first filter portion 36 that is bounded by these four points is referred to below as LIPO, and the area of that portion $A_{LIPO}$. Further, let M be the point of the incident light beam projection 44 that crosses the X-axis in a neutral state (i.e., such that $L_0$=M), and let Q be the point of the incident light beam projection that crosses the Y-axis in a neutral state (i.e., such that $P_0$=Q). The portion of the filter bounded by points O, M, Q, and I is referred to below and MIQO, and the area of that portion $A_{MIQO}$. In a neutral state, $A_{LIPO}$=$A_{MIQO}$. Thus, $A_{LIPO\_0}$=$A_{MIQO}$. Still further, the triangle bounded by points O, P, and Q is referred to as QPO, and its area $A_{QPO}$. The triangle bounded by points O, L, and M is referred to as MOL and its area $A_{MOL}$.

The difference between $A_{LIPO}$ and $A_{MIQO}$ (and thus, the difference in the light incident on the first filter portion 36 between a neutral state and a twisted state) is a function of the areas of QPO and MOL as shown in equation (10) below:

$$A_{LIPO} - A_{MIQO} = A_{MOL} - A_{QPO} \tag{10}$$

The areas of QPO and MOL are, respectively, functions of the rotation angle γ, as shown in equations (11) and (12) below:

$$A_{MOL} = \frac{|OM|^2 \tan(\gamma)}{2} = \frac{A^2 \tan(\gamma)}{2} \tag{11}$$

$$A_{QPO} = \frac{|OP|^2 \tan(\gamma)}{2} = \frac{B^2 \tan(\gamma)}{2} \tag{12}$$

where OM and OP are the vectors between points O and M and O and P, respectively.

Accordingly, the difference between $A_{LIPO}$ and $A_{MIQO}$ is also a function of the rotation angle γ, as shown by reducing equations (10)-(12) to equation (13) below:

$$A_{LIPO} - A_{MIQO} = \frac{(A^2 - B^2)\tan(\gamma)}{2} \tag{13}$$

At angles of γ of much less than one radian, such as 0.2 radians or less, for example, tan(γ)≈γ, allowing equation (13) to be further reduced to equation (14) below, which may be computationally more efficient:

$$A_{LIPO} - A_{MIQO} = \frac{(A^2 - B^2)\gamma}{2} \tag{14}$$

It should be noted that equation (14) (or its equivalent) would not work for circular incident light because circular incident light does not change across the filter segments 36, 38, 40, 42 as it rotates due to twist. Accordingly, in an embodiment, a rectangular or elliptical (non-circular) or another rotationally asymmetric beam projection shape from the light source 28 may be used to detect twist.

Equation (14) above is the contribution of twist to the differential amount of light incident on the first filter portion. The same analysis may be performed for the second, third, and fourth filter portions. Accordingly, equation (14) may be added to equation (4) above (which contains the contributions of X-axis and Y-axis shifting to the differential amount of light incident on a given filter portion) to arrive at equation (15) below, which gives the total differential amount of light incident on the optical receiver for three degrees of freedom (i.e., X-axis shift, Y-axis shift, and twist):

$$V_{det\_i} = V_{det\_i0} + (v_{1i} - v_{2i} - v_{3i} + v_{4i})(B\Delta x) + \tag{15}$$
$$(v_{1i} + v_{2i} - v_{3i} - v_{4i})(A\Delta y) + (v_{1i} - v_{2i} + v_{3i} - v_{4i})\frac{(A^2 - B^2)}{2}\gamma$$

As in the two degrees-of-freedom example, the angles α, β of deflection in the X- and Y-directions, respectively, are proportional to Δx and Δy. Series of equations (15) will result in three equations (one for blue light, one for red, and one for green) and three unknowns (Δx, Δy, and γ). Accordingly, Δz, Δy, and γ (i.e., both the magnitude and direction thereof) may be determined according to known systems and methods for solving a system of several equations with several unknowns.

Equation (15) can be solved with high accuracy for Δx, Δy, and γ if, in an embodiment, the singular values of the 3×3 coefficient matrix given by the right-hand side of equation (15) do not differ by more than a factor of about 4. The coefficient matrix, referred to below as $v_{mat2}$ relates the values of BΔx, AΔy, and $(A^2-B^2)\gamma$ and $V_{det\_R}$, $V_{det\_G}$, and $V_{det\_B}$, and is shown as matrix (16) below:

$$v_{mat2} = \begin{bmatrix} v_{RX} & v_{RY} & v_{R\gamma} \\ v_{BX} & v_{BY} & v_{B\gamma} \\ v_{GX} & v_{GY} & v_{G\gamma} \end{bmatrix} \tag{16}$$

where $v_{RX}$=$v_{1R}$−$v_{2R}$−$v_{3R}$+$v_{4R}$, $v_{RY}$=$v_{1R}$+$v_{2R}$−$v_{3R}$+$v_{4R}$, $V_{R\gamma}$=$v_{1R}$−$v_{2R}$+$v_{3R}$−$v_{4R}$, and so on. Once again, it should be noted that in $v_{mat2}$, the subscript X refers not to a variable color of light, but to the X-direction shown in FIGS. 3-5. In a different embodiment, the values of $v_{mat2}$ may differ by more than a factor of 4 while permitting a highly accurate determination of Δx, Δy, and γ.

Once Δx, Δy, and γ are determined, the deflection and twist of the shaft 12 over the optical path 44 may be determined. In order to do so, four receiver output calibration parameters are required for each light color: (a) the zero-deflection, zero-twist output of the receiver $V_{det\_i0}$; (b) the receiver output $V_{det\_i\_\alpha\_cal}$ for a selected deflection $\alpha_{cal}$ in a first direction (i.e., along the X-axis in FIGS. 3-5); (c) the receiver output $V_{det\_i\_\beta\_cal}$ for a selected deflection $\beta_{cal}$ in a second direction (i.e., along the Y-axis in FIGS. 3-5); and (d) receiver output $V_{det\_i\_\gamma\_cal}$ for a selected twist $\gamma_{cal}$. The resulting calibration matrix $C_{mat}$, shown below as matrix (15), can be used according to equation (16), also shown below, to solve $\alpha$, $\beta$, and $\gamma$ given receiver output $V_{det\_i}$ for red, blue, and green light:

$$C_{mat} = \begin{bmatrix} \dfrac{V_{det\_R\_\alpha\_cal} - V_{det\_R0}}{\alpha_{cal}} & \dfrac{V_{det\_R\_\beta\_cal} - V_{det\_R0}}{\beta_{cal}} & \dfrac{V_{det\_R\_\gamma\_cal} - V_{det\_R0}}{\gamma_{cal}} \\ \dfrac{V_{det\_B\_\alpha\_cal} - V_{det\_B0}}{\alpha_{cal}} & \dfrac{V_{det\_B\_\beta\_cal} - V_{det\_B0}}{\beta_{cal}} & \dfrac{V_{det\_B\_\gamma\_cal} - V_{det\_B0}}{\gamma_{cal}} \\ \dfrac{V_{det\_G\_\alpha\_cal} - V_{det\_G0}}{\alpha_{cal}} & \dfrac{V_{det\_G\_\beta\_cal} - V_{det\_G0}}{\beta_{cal}} & \dfrac{V_{det\_G\_\gamma\_cal} - V_{det\_G0}}{\gamma_{cal}} \end{bmatrix} \quad (15)$$

$$\begin{pmatrix} \alpha \\ \beta \\ \gamma \end{pmatrix} = \text{inv}(C_{mat}) \begin{pmatrix} V_{det\_R} - V_{det\_R0} \\ V_{det\_B} - V_{det\_B0} \\ V_{det\_G} - V_{det\_G0} \end{pmatrix} \quad (16)$$

Once $\alpha$, $\beta$, and $\gamma$ have been solved, the external forces resulting in deflection and twisting of the shaft 12 can be calculated according to the principles of elastostatics described above.

Figure 6:
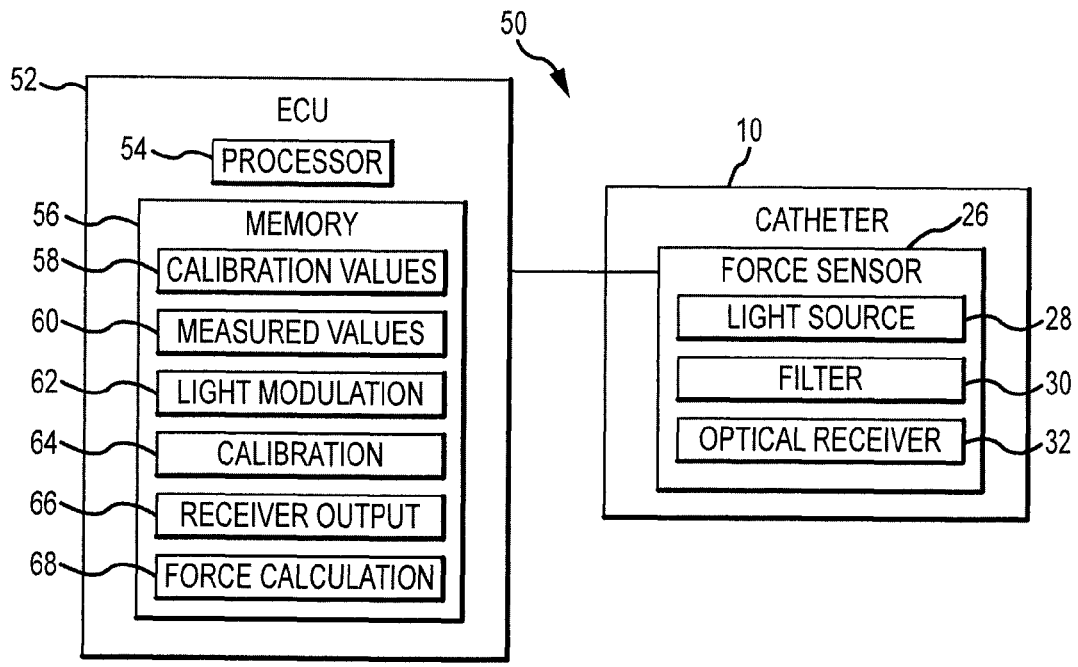
FIG. 6 is a schematic view of a system that may be used for determining deformation characteristics and external forces on the elongate medical device of FIG. 1 using an optical force sensor.

FIG. 6 is a schematic view of a system 50 for determining the deformation (e.g., deflection, twisting, and/or other deformation) of a device, such as catheter shaft 12, and corresponding forces applied to the device. In an embodiment, the system 50 may include the force sensor 26, including the light source 28, the optical filter 30, and the optical receiver 32, disposed in or coupled to the catheter 10 and an electronic control unit (ECU) 52. The ECU 52 may include a processor 54 configured to execute instructions, code, or programming stored in memory 56. The processor 54 may also be configured to store measurements and calibration parameters in the memory 56, in an embodiment.

The memory 56 may include portions for storing values for use in calculating deformation of the catheter 10 (e.g., the distal end portion 14 of the shaft 12 of the catheter 10), calculating the forces indicated by deformation of the catheter 10, and/or other operations. In an embodiment, such portions may include a calibration values portion 58 and a measured values portion 60. The processor may be configured to write values to and read values from the calibration values and measured values portions 58, 60 as described below.

The memory 56 may include light modulation instructions 62 for operating or modulating the light source 28. Accordingly, the processor 54 may execute the light modulation instructions 62 to cause the light source 28 to output light of different colors, frequencies, and/or frequency bands in a predetermined sequence, i.e., in a time-multiplexed fashion. A light sequence according to the light modulation instructions 62 may include a number of time segments, with a single color, frequency, or frequency band of light output during each time segment, such that the number of segments in the timing sequence is equal to the number of colors, frequencies, or frequency bands of light that the light source 28 may output. Thus, in an embodiment, such a sequence may include the light source 28 outputting red light for a first period of time, then blue light for a second period of time, then green light for a third period of time, then red light again for the first period of time, and so on. The periods of time of each segment of the sequence may be equal to each other, in an embodiment. In another embodiment, the periods of time of the segments of the sequence may be different from each other to facilitate identification of time intervals when a specific color, frequency, and/or frequency band is produced.

The memory 56 may further include calibration instructions 64 for populating the calibration values portion 58 with appropriate values. Such population may involve calculating calibration parameters and/or retrieving calibration parameters from an external source and storing those parameters to the calibration values portion 58. Accordingly, the processor 54 may execute the calibration instructions 64 to determine and/or receive calibration parameters. The calibration parameters may include, but are not limited to, the calibration values discussed above, such as $\mu_\alpha$, $\mu_\beta$, $\alpha_{cal}$, $\beta_{cal}$, $\gamma_{cal}$, $V_{det\_R\_\alpha\_cal}$, $V_{det\_R\_\beta\_cal}$, and $V_{det\_R\_\gamma_{cal}}$. In an embodiment, calibration parameters may be calculated by the processor 54 by receiving one or more signals from the optical receiver 32 during a calibration procedure as noted above. In the same or a different embodiment, calibration parameters may be input by a user and received by the processor 54, or pre-stored and read by the processor 54 from the memory 56 or from some other data storage device (e.g., an EEPROM or other removable memory coupled with the catheter 10).

The memory 56 may further include receiver output instructions 66 for receiving and storing outputs from the optical receiver 32. Accordingly, the processor 54 may execute the receiver output instructions 66 to receive a signal from the optical receiver 32 indicative of the amount of light detected by the receiver 32, process the signal to determine the amount of light detected by the receiver 32, and associate that light amount with a particular color of light according to the output of the light source 28 known to the processor 54. The processor 54 may then store the light amount value or other data according to the signal in the measured values portion 60 of the memory 56, determine deflection, twisting, or compression of the catheter as described below, or perform some alternative or additional operations with the signal or light amount value.

The memory 56 may further include, and the processor 54 may be configured to execute, force calculation instructions 68 for calculating one or more parameters of a deflection, twist, or other deformation of a portion of the catheter 10. For example, in an embodiment, the force calculation instructions 68 may include steps to construct and solve a series of equations according to equations (4) and/or (15) above to determine one or more deformation parameters or characteristics (e.g., deflection angle $\alpha$ along a first axis, deflection angle $\beta$ along a second axis, and twist angle $\gamma$ about a third axis). Accordingly, the force calculation instructions 68 may include steps involving the use of the values stored in the calibration value measured value portions 56, 58 for use in one or more equations. The force calculation instructions 68 may further include steps to determine a force applied to the exterior of the catheter 10 according to the determined deformation parameters. For example, in an embodiment, the force calculation instructions 68 may include steps to construct and solve a series of equations according to the linear elasticity equations (7)-(9) above.

The processor 54 may be configured, in an embodiment, to execute the calibration instructions 64 at the beginning of a medical procedure using the catheter 10. The processor 54 may be further configured to execute the light modulation, receiver output, and force calculation instructions 62, 66, 68 continuously throughout a medical procedure to monitor the external forces applied to the catheter 10. If the processor 54 detects a force or set of forces indicative of an undesirable position, shape, or orientation of the catheter 10 relative to tissue (e.g., excess force indicating the possibility of tissue puncture), the ECU 52 or other device may produce a visual, auditory, or other output to inform the physician operating the catheter 10 of the undesirable position, shape, or orientation. The ECU 52 may additionally or alternatively produce an output to indicate sufficient contact between the catheter 10 (e.g., the distal tip 24) and tissue to perform a particular procedure. For example, such a signal may be received by an ablation system during an ablation procedure or a mapping system during a mapping procedure.

Detecting external forces on the catheter 10 with the optical force sensor 26 and the system 50 may be preferable to known devices, systems, and methods because of the relatively low complexity and cost of the sensor 26. Only a single light source 28 and a single receiver 32 may be required, in an embodiment, to detect external forces with three or more degrees-of-freedom; this contrasts with many known systems, which may require a sensor per degree-of-freedom. Furthermore, the components of the sensor 26 may be very small in size, and thus may occupy little space within the catheter 10 and may maximize the amount of space available for other sensors, wiring, lumens, and other desirable features.

The sensor 26 and/or system 50 may also find use in a remote catheter guidance system (RCGS) including, for example, robotic guidance and control of one or more catheters. An exemplary system is described in U.S. patent application publication no. 2009/0247993, hereby incorporated by reference in its entirety as though fully set forth herein.

Figure 7:
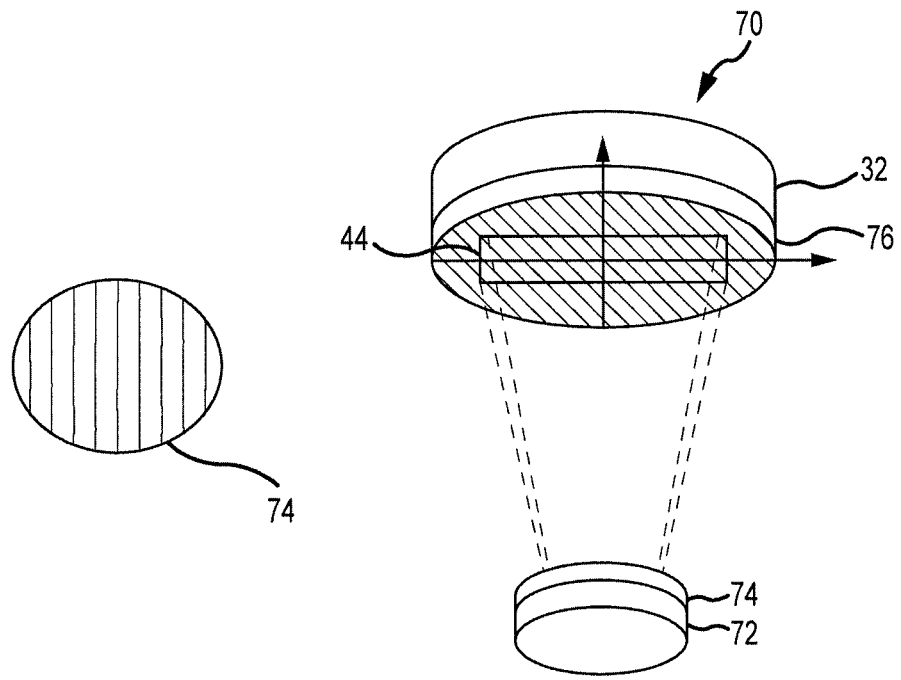
FIG. 7 is a diagrammatic view of another embodiment of an optical force sensor that may be used with the elongate medical device of FIG. 1.

FIG. 7 is a diagrammatic view of an alternate embodiment of an optical force sensor 70. The force sensor 70 may be used instead of, or in addition to, the force sensor 26 in the system 50 of FIG. 6 and in the other applications described herein. With continued reference to FIG. 7, the force sensor 70 may include a light source 72, a first polarizing filter 74, a second polarizing filter 76, and an optical receiver 32. The light source 72 may be configured, in an embodiment, to provide light of a single frequency. The first polarizing filter 74 may be rigidly coupled to the light source 72 to linearly polarize that light in a first direction. The second polarizing filter 76 may be rigidly coupled to the optical receiver 32 to polarize the light in a second direction that is offset by a selected amount from the first direction. In an embodiment, the second direction may be offset from the first direction by about forty-five degrees (45°).

In a neutral state, the optical receiver 32 may detect a first amount of light. As the catheter 10 deforms, and the incident light 44 on the second filter 76 shifts or rotates, the optical receiver 32 may detect a second amount of light. Depending on the relative shapes and orientations of the first and second filters 74, 76, the first amount detected by the optical receiver 32 (in a neutral state) and the second amount detected by the optical receiver 32 (in a non-neutral state) may be different. For example, in the embodiment shown in FIG. 7, in which the second filter 76 is substantially the same shape and size as the first filter 74, but the polarization of the second filter 76 is offset from the polarization of the first filter 74 by about forty-five degrees (45°), as the light source 72 rotates relative to the receiver 32, the amount of light detected by the receiver 32 will either increase (if the rotation decreases the angular offset between the filters 74, 76) or decrease (if the rotation increases the angular offset between the filters 74, 76). Accordingly, the embodiment illustrated in FIG. 7 may be particularly useful for detecting twist of the shaft 12. Other arrangements of the filters 74, 76 may be used (e.g., multiple filter segments with different polarizations in one or both of the filters 74, 76, relative size or shape differences between the filters 74, 76, etc.) to better detect other deformations of the shaft 12.

Figure 8:
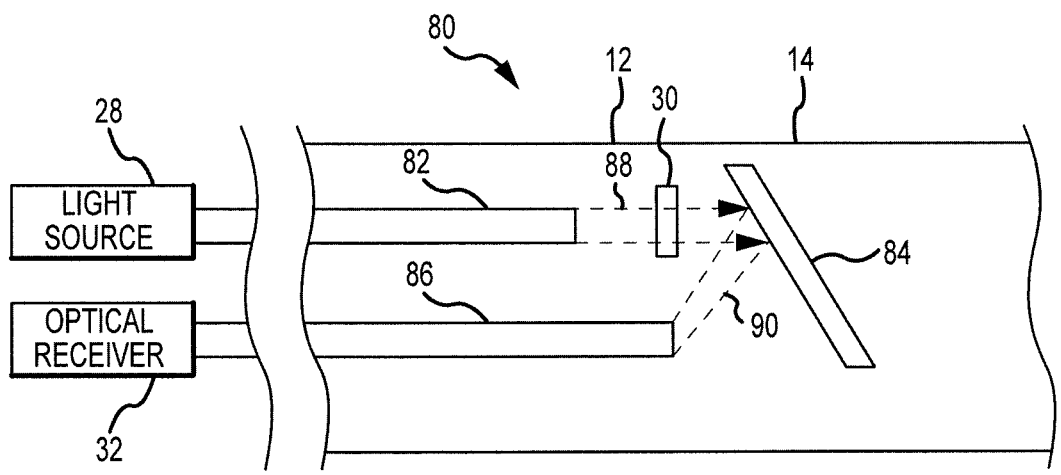
FIG. 8 is a diagrammatic view of another embodiment of an optical force sensor that may be used with the elongate medical device of FIG. 1.

FIG. 8 is a diagrammatic view of another alternate embodiment of an optical force sensor 80, based on the same principles as the force sensor 26 and system 50 illustrated and described above with respect to FIGS. 2-6. Accordingly, the sensor 80 may be used in addition to or instead of the sensor 26 in the various systems and applications described herein. With continued reference to FIG. 8, the sensor 80 may include the light source 28, a first optical fiber 82, the filter 30, a mirror 84, a second optical fiber 86, and the optical receiver 32. The light source 28, filter 30, and optical receiver 32 may function substantially as described above with respect to the sensor 26. Furthermore, the sensor 80 may also be used in conjunction with the system 50, in addition to or instead of the sensor 26, in substantially the same manner described above in conjunction with FIG. 6 with respect to the system 50 and the sensor 26.

Referring again to FIG. 8, both the light source 28 and the receiver 32 may be disposed outside the shaft 12, while the optical fibers 82, 86, the filter 30, and the mirror 84 may be disposed inside the shaft 12. More particularly, the filter 30 and mirror 84 may be disposed within the distal end portion 14 of the shaft 12. The first optical fiber 82 may transmit a light beam generated by the light source 28 and project the beam along a first optical path 88 extending through the filter 30 to the mirror 84, which may reflect the light along a second optical path 90 to the second optical fiber 86 for transmission to the optical receiver 32. In an embodiment, a lens (not shown) may be placed in the second optical path 90 to focus the light beam reflected by the mirror 84 into the second optical fiber 86. Rather than measuring shaft deformation between the light source 28 and the receiver 32, the sensor may be used to measure shaft deformation (and the accompanying forces on the shaft 12) between the first optical fiber 82 and the filter 30. Because the light source 28 and receiver 32 may be located outside the shaft 12, in an embodiment, the sensor 80 may further reduce the space occupied within the shaft 12 as compared to the sensor 26.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus for detecting deformation of an elongate body, the apparatus comprising:
 a light source configured to provide light of multiple frequencies;
 an optical receiver configured to receive light from said light source; and
 a filter disposed between said light source and said optical detector, said filter comprising multiple segments, each of said segments configured to filter light at one of said frequencies so as to alter the amount of light incident on said optical receiver, wherein at least two of said segments filter light at the same frequency, wherein said optical receiver is configured to receive light from all of the multiple segments of the filter;
 wherein a total amount of light received by said optical receiver is indicative of deformation of the elongate body.

2. The apparatus of claim 1, wherein said light source is configured to provide said light of multiple frequencies in a predetermined sequence.

3. The apparatus of claim 1, wherein said filter comprises a first number of segments, said light source is configured to provide light of a second number of frequencies, and said first number is greater than or equal to said second number.

4. The apparatus of claim 3, wherein said filter comprises at least four segments.

5. The apparatus of claim 4, wherein said light source is configured to provide light at least three frequencies.

6. The apparatus of claim 1, wherein light of all of said multiple frequencies is in the visible spectrum.

7. The apparatus of claim 1, wherein said light source comprises a multi-color LED.

8. The apparatus of claim 1, wherein said optical detector responds substantially the same to light at each of said multiple frequencies.

9. An elongate medical device, comprising:
 a handle;
 an elongate shaft having a proximal end portion and a distal end portion, said proximal end portion coupled with said handle, said elongate shaft configured for insertion into a body of a patient;
 a light source configured to provide light of multiple frequencies along an optical path, said optical path disposed at least in part within said distal end portion of said elongate shaft and contained completely within the elongate medical device;
 an optical receiver configured to receive light projected along said optical path; and
 a filter disposed in said optical path, said filter comprising multiple segments, each of said segments configured to filter light at one of said frequencies so as to reduce the amount of light incident on said optical receiver.

10. The elongate medical device of claim 9, wherein said light source and said optical receiver are disposed in said distal end portion of said shaft.

11. The elongate medical device of claim 10, wherein said light source is disposed about 0.5 inches to about 2.0 inches from said optical receiver.

12. The elongate medical device of claim 9, wherein said optical path is sealed from fluid.

13. The elongate medical device of claim 9, wherein at least one of said light source and said optical receiver is disposed within about two inches of a distal tip of said shaft.

14. A system for assessing force on a medical device, the system comprising:
 an electronic control unit (ECU) configured to:
  couple to a medical device;
  operate a light source to emit light of different frequencies in a predetermined sequence, said sequence comprising two or more time segments, said light source outputting a different frequency of light in each segment;
  receive a signal generated by an optical receiver responsive to said light output by said light source; and
  process said signal in accordance with said predetermined sequence to determine an external force applied to the medical device and a magnitude and direction of a twisting of the medical device.

15. The system of claim 14, wherein said ECU is configured to process said signal in accordance with said predetermined sequence to determine a magnitude and a direction of a deflection of the medical device.

16. The system of claim 14, wherein said ECU is configured to process said signal in accordance with said predetermined sequence by determining an amount of light received by said optical detector at multiple different segments of said sequence.

17. The system of claim 16, wherein a number of time segments in said sequence is equal to a number of frequencies in said multiple frequencies.

18. The system of claim 14, wherein two of said time segments have different respective durations.

19. The system of claim 14, wherein said ECU is configured to process said signal in accordance with said predetermined sequence to determine a magnitude and a direction of said external force.

* * * * *